US005549631A

United States Patent [19]

Bonutti

[11] Patent Number: 5,549,631
[45] Date of Patent: *Aug. 27, 1996

[54] METHOD OF CLOSING DISCONTINUITY IN TISSUE

[76] Inventor: Peter M. Bonutti, 1303 W. Evergreen Plz., Effingham, Ill. 62401

[*] Notice: The term of this patent shall not extend beyond the expiration date of Pat. No. 5,464,260.

[21] Appl. No.: 446,333

[22] Filed: May 22, 1995

Related U.S. Application Data

[60] Division of Ser. No. 207,297, Mar. 7, 1994, Pat. No. 5,464,426, which is a continuation-in-part of Ser. No. 62,295, May 14, 1993, Pat. No. 5,403,348.

[51] Int. Cl.⁶ ........................................ A61B 17/04
[52] U.S. Cl. .................................................. 606/232
[58] Field of Search .............................. 606/72–74, 139, 606/144, 145, 151, 220, 232; 24/115 H, 122.6

[56] References Cited

U.S. PATENT DOCUMENTS

| | | |
|---|---|---|
| 2,199,025 | 4/1940 | Conn . |
| 3,625,220 | 12/1971 | Engelsher . |
| 3,648,705 | 3/1972 | Lary . |
| 4,210,148 | 7/1980 | Stivala . |
| 4,235,238 | 11/1980 | Oglu et al. . |
| 4,409,974 | 10/1983 | Freedland . |
| 4,448,194 | 5/1984 | DiGiovanni et al. . |
| 4,669,473 | 6/1987 | Richards et al. . |
| 4,741,330 | 5/1988 | Hayhurst . |
| 4,750,492 | 6/1988 | Jacobs . |
| 4,823,794 | 4/1989 | Pierce . |
| 4,898,156 | 2/1990 | Gatturna et al. . |
| 4,968,315 | 11/1990 | Gatturna . |
| 5,009,663 | 4/1991 | Broome . |
| 5,037,422 | 8/1991 | Hayhurst et al. . |
| 5,041,129 | 8/1991 | Hayhurst et al. . |
| 5,046,513 | 9/1991 | Gatturna et al. . |
| 5,053,047 | 10/1991 | Yoon . |
| 5,100,417 | 3/1992 | Cerier et al. . |
| 5,102,421 | 4/1992 | Anspach, Jr. . |
| 5,123,520 | 6/1992 | Cope . |
| 5,141,520 | 8/1992 | Goble et al. . |
| 5,156,616 | 10/1992 | Meadows et al. . |
| 5,176,682 | 1/1993 | Chow . |

Primary Examiner—Gary Jackson
Attorney, Agent, or Firm—Tarolli, Sundheim, Covell, Tummino & Szabo

[57] ABSTRACT

When a discontinuity in body tissue is to be closed, a suture is inserted through openings in a plurality of anchors. A thin elongated member, such as a needle or K-wire, is also inserted through the openings in the anchors. The thin elongated member is then inserted through the body tissue at a first location along one side of the discontinuity in the body tissue. A first anchor is then pushed through the body tissue from the inner side of the body tissue to the outer side of the body tissue with the suture extending through the opening in the anchor. The thin elongated member is then withdrawn from the body tissue and subsequently inserted through the body tissue at a second location disposed along the second or opposite side of the discontinuity. The next succeeding anchor in the array of anchors on the suture and thin elongated member is then pushed through the body tissue at the second location. Pulling on the suture presses the anchors against the body tissue and presses the body tissue together. The anchors may be pushed through the body tissue with a pusher member or by pushing the anchors against each other.

9 Claims, 4 Drawing Sheets

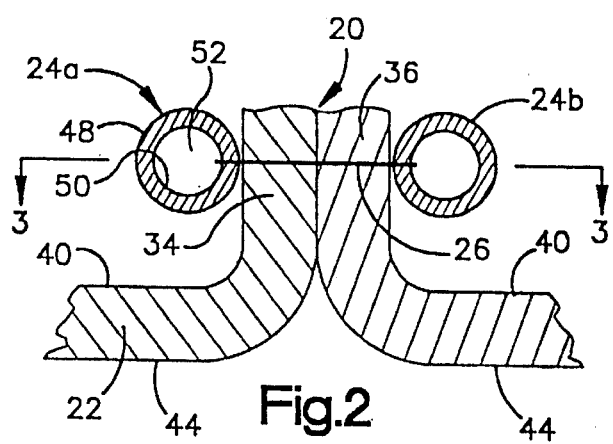
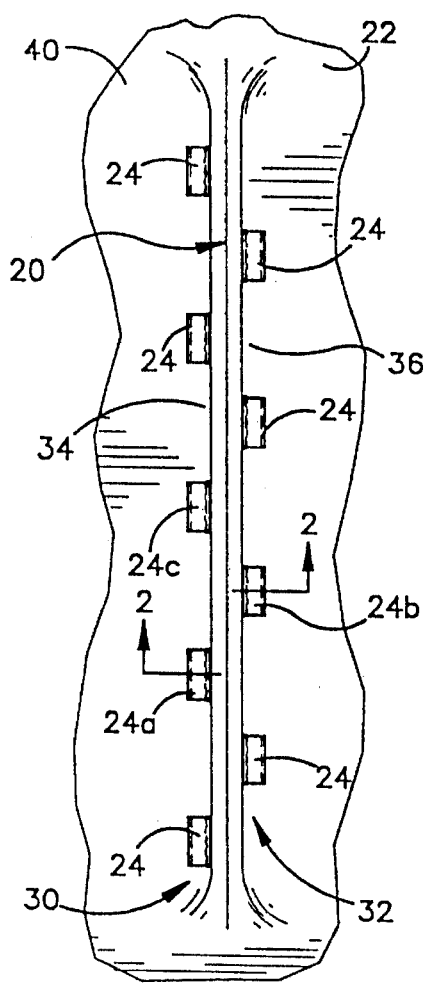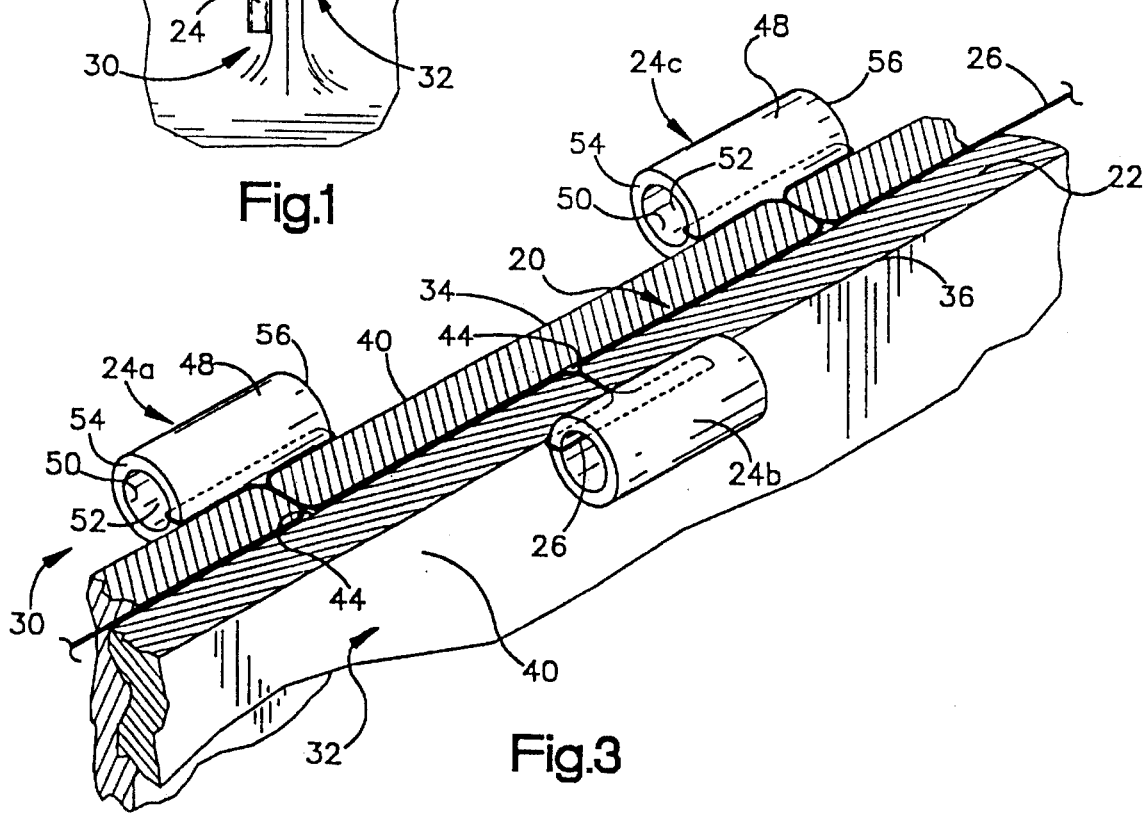

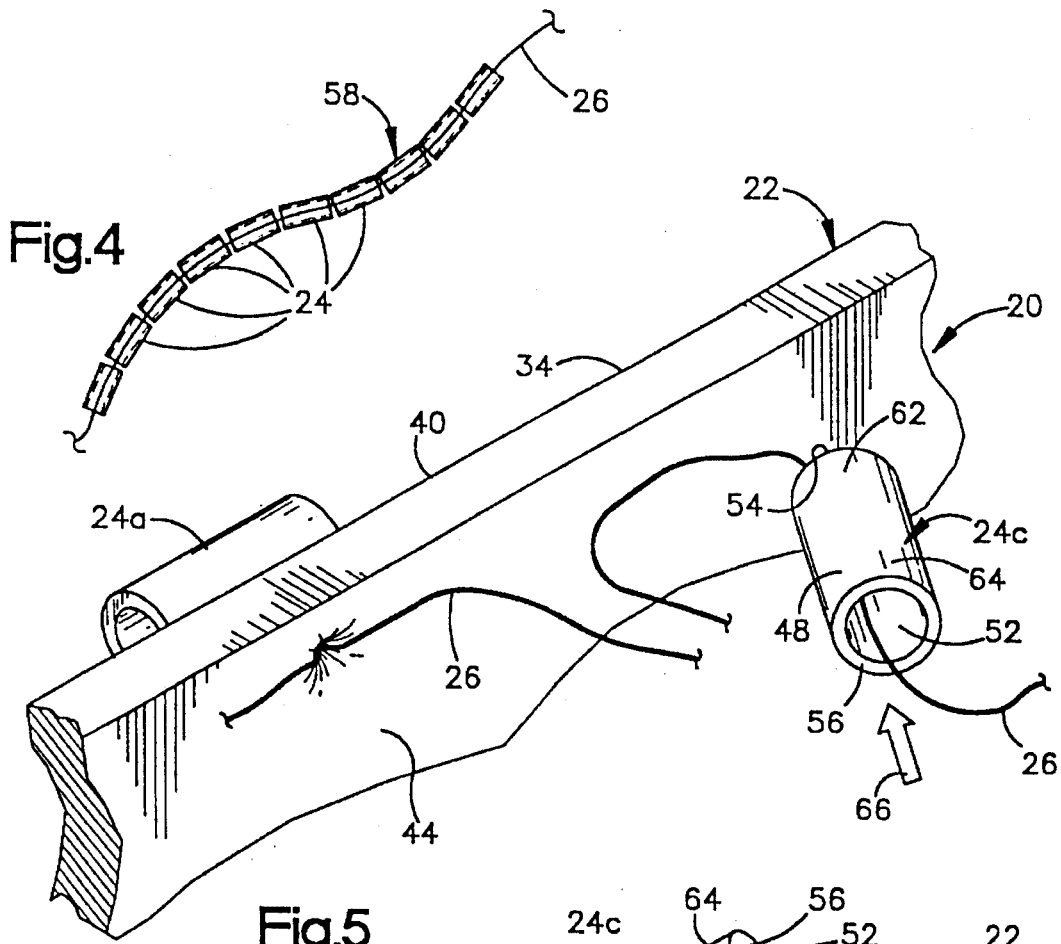
Fig.4
Fig.5
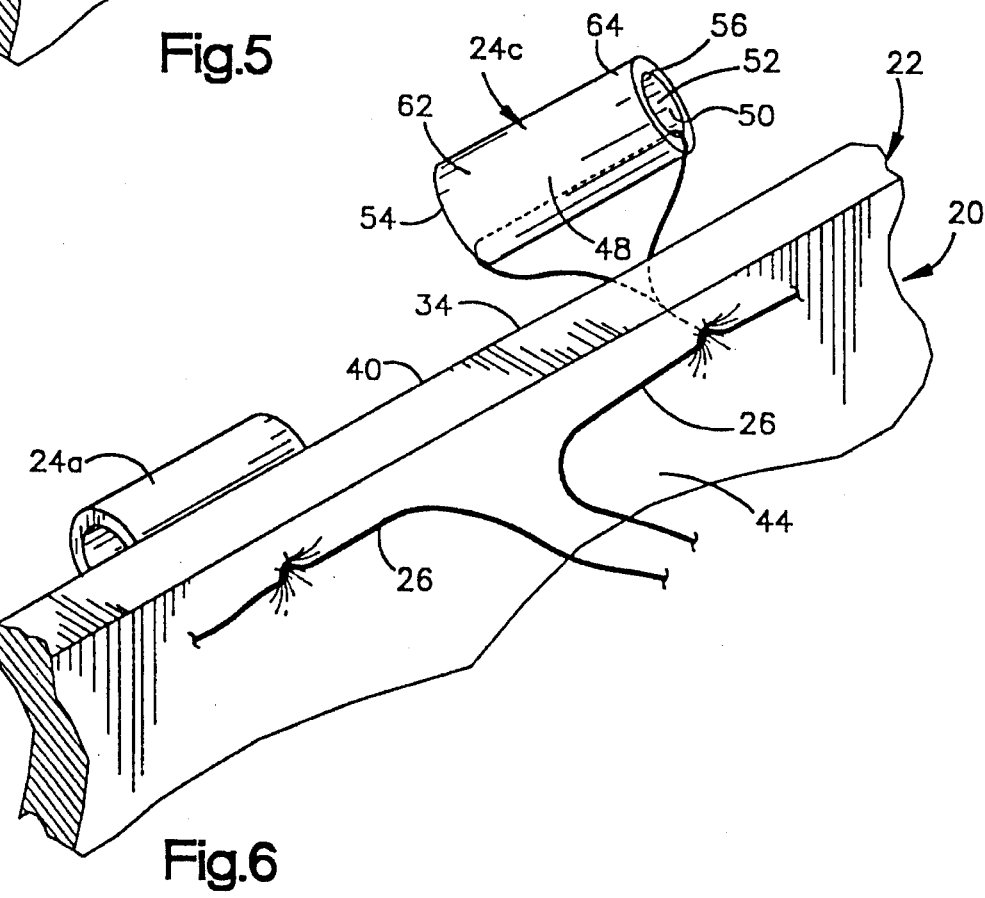
Fig.6

METHOD OF CLOSING DISCONTINUITY IN TISSUE

RELATED APPLICATION

This application is a divisional of U.S. patent application Ser. No. 08/207,297, filed on Mar. 7, 1994, now U.S. Pat. No. 5,464,426 by Peter M. Bonutti and entitled METHOD OF CLOSING DISCONTINUITY IN TISSUE. The aforementioned U.S. patent application Ser. No. 08/207,297 is itself a continuation-in-part of U.S. patent application Ser. No. 08/062,295 filed May 14, 1993, now U.S. Pat. No. 5,403,348 by Peter M. Bonutti and entitled SUTURE ANCHOR and of copending patent application Ser. No. 08/207,297 filed Mar. 7, 1994 by Peter M. Bonutti and entitled METHOD OF CLOSING DISCONTINUITY IN TISSUE. The benefit, under Title 35, United States Code, ¶120, of the aforementioned application is hereby claimed.

BACKGROUND OF THE INVENTION

The present invention relates to a new and improved method of closing a discontinuity in body tissue.

A method and apparatus for closing a discontinuity in body tissue is disclosed in U.S. Pat. No. 4,448,194 issued May 15, 1984. This patent discloses the use of a fastener to close a discontinuity, such as a wound or incision, in body tissue. The fastener includes a filament which extends between rod-shaped heads of the fastener.

Another method of closing a discontinuity in body tissue is disclosed in U.S. Pat. No. 4,823,794 issued Apr. 25, 1989. This patent discloses the use of a pair of pledgets in combination with a suture. The pledgets are disposed along opposite sides of the discontinuity in the body tissue and are interconnected by a suture. The suture is drawn tight to close the space between opposite sides of the discontinuity and is then tied to hold the pledgets in place.

SUMMARY OF THE INVENTION

The present invention provides a new and improved method of closing a discontinuity in body tissue. When a discontinuity in body tissue is to be closed, a suture is inserted through openings in anchors to provide a series of anchors on the suture. In addition, a thin elongated member may be inserted through the openings in the anchors.

The thin elongated member is then inserted through body tissue at a first location disposed along a first side of the discontinuity. A first anchor is then pushed through the body tissue with the suture extending through the opening in the first anchor. The thin elongated member is then inserted through body tissue at a second location disposed along a second side of the discontinuity. A second anchor is pushed through the body tissue with the suture extending through the opening in the second anchor.

BRIEF DESCRIPTION OF THE DRAWINGS

The foregoing and other features of the invention will become more apparent upon a consideration of the following description taken in connection with the accompanying drawings, wherein:

FIG. 1 is a schematicized plan view of a body tissue discontinuity which has been closed with a suture and a plurality of anchors;

FIG. 2 is a sectional view, taken generally along the line 2—2 of FIG. 1, illustrating the relationship between anchors disposed along opposite sides of the discontinuity and a suture which extends through openings in the anchors;

FIG. 3 is a schematicized sectional view, taken generally along the line 3—3 of FIG. 2, further illustrating the relationship of the anchors and suture to the discontinuity in the body tissue;

FIG. 4 is an illustration depicting the manner in which an array or series of anchors is positioned on a suture in preparation to undertake the closing of a discontinuity in body tissue;

FIG. 5 is a schematicized illustration depicting the manner in which an anchor is oriented relative to an inner side of the body tissue prior to being pushed through the body tissue;

FIG. 6 is a schematic illustration depicting the manner in which an anchor is positioned relative to the body tissue by pulling on a suture after the anchor has been pushed through the body tissue;

DESCRIPTION OF SPECIFIC PREFERRED EMBODIMENTS OF THE INVENTION

Closure

Figure 7:
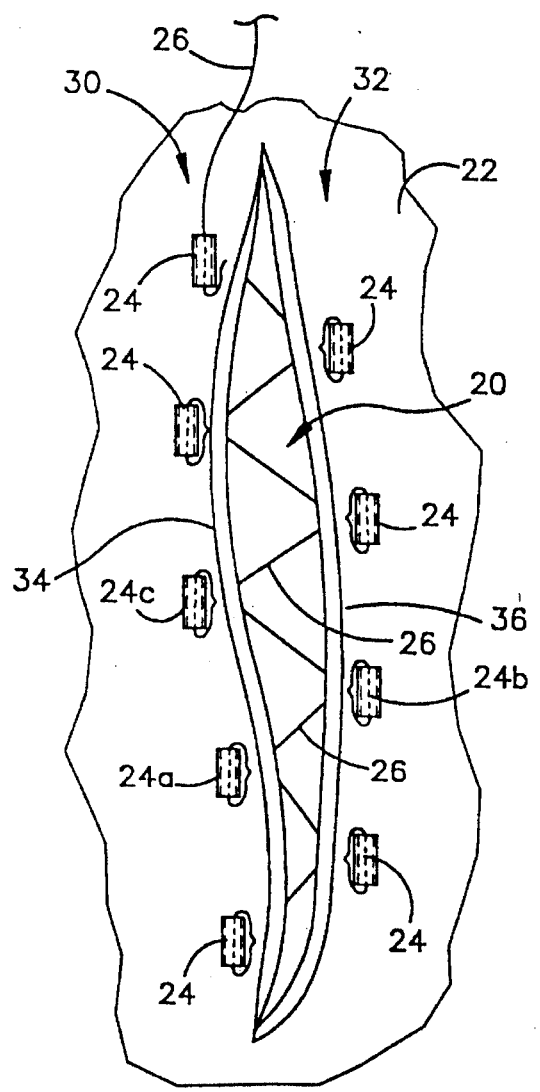
FIG. 7 is a schematic illustration depicting the manner in which a discontinuity in body tissue is loosely closed prior to pulling on a suture.

A discontinuity 20 (FIG. 1) in body tissue 22 is closed by a plurality of anchors 24 which are interconnected by a suture 26 (FIG. 2). The discontinuity 20 may be a wound or incision in the body tissue 22. The anchors 24 are disposed in arrays 30 and 32 (FIG. 1) along opposite sides of the discontinuity 20. Thus, the array 30 of anchors 24 is disposed along the left side 34 of the body tissue discontinuity 20 and the array 32 of anchors is disposed along the right side 36 of the discontinuity. The discontinuity 20 may be an incision, wound or other opening in the body tissue 22.

The suture 26 extends back and forth across the discontinuity 20 between the left and right arrays 30 and 32 of anchors 24. Thus, the suture 26 extends through an opening in an anchor 24a (FIG. 1) on the left side of the discontinuity 20. The suture 26 extends from the anchor 24a across the discontinuity 20 to an anchor 24b on the right side of the discontinuity. The suture 26 extends through an opening in the anchor 24b on the right side of the discontinuity 20. The suture 26 extends from the anchor 24b across the discontinuity 20 to an anchor 24c on the left side 34 of the discontinuity.

Thus, a single suture 26 extends back and forth across the discontinuity 20 between each of the anchors 24 in the left and right arrays 30 and 32 of anchors. Each of the anchors 24 along the left side 34 of the discontinuity 20 is offset longitudinally along the discontinuity from adjacent anchors along the right side 36 of the discontinuity.

Tension in the suture 26 presses the anchors 24 against the opposite sides 34 and 36 of the discontinuity 20 (FIG. 3). Thus, the suture 26 applies force against the anchor 24a to press the anchor against an outer side surface 40 of the body tissue 22 on the left side 34 of the discontinuity 20. Similarly, the suture 26 presses the anchor 24b against the outer side surface 40 of the body tissue 22 on the right side 36 of the discontinuity 34.

The force applied against the outer side surface 40 of the body tissue 22 by the anchors 24 presses an inner side surface 44 (FIGS. 2 and 3) on the body tissue 22 on the left side 34 of the discontinuity 20 against the inner side surface of the body tissue on the right side 36 of the discontinuity (FIG. 3). The suture 26 extends between the inner side surface 44 on the left and right sides 34 and 36 of the discontinuity 20. Tension in the suture 26 pulls the anchors 24a and 24c toward the right (as viewed in FIG. 3) and pulls the anchor 24b toward the left. This results in surface areas on the inner side surface 44 of the body tissue 22 on opposite sides of the discontinuity 20 being pressed together.

The anchors 24 (FIGS. 2 and 3) all have the same hollow cylindrical configuration. Thus, the anchor 24a has a cylindrical outer side surface 48 which is pressed against the outer side surface 40 of the body tissue 20 by the suture 26. The anchor 24a has a cylindrical inner side surface 50 which defines a cylindrical opening or passage 52 through which the suture 26 extends. The anchor 24a has a pair of parallel end surfaces 54 and 56 across which the suture 26 extends. The anchor 24a has the same construction as is disclosed in U.S. patent application Ser. No. 08/062,295 filed May 14, 1993 by Peter M. Bonutti and entitled "Suture Anchor". Of course, the anchors 24 could have a different construction if desired.

The discontinuity 20 (FIG. 1) is closed by using a single suture and nine identical anchors 24. However, it is contemplated that the number of anchors which are used to close a discontinuity in body tissue 22 will depend on the length of the discontinuity. Thus, any desired number of anchors may be used. For example, only two anchors 24 may be required to close a relatively small discontinuity 20 while more than nine anchors may be required to close a relatively large discontinuity.

Although it is preferred to use anchors 24 having a hollow cylindrical construction, anchors having a different construction could be used if desired. Regardless of the construction of the anchor 24, a suture 26 would extend through an opening in each of the anchors and urge them toward each other to press the body tissue along the left and right sides 34 and 36 of the discontinuity together.

The suture 26 may be a thread, wire or other biocompatible material. The suture 26 may be formed of a material which is absorbable or nonabsorbable by the body tissue 22. The body tissue 22 may be any desired portion of the human body. The body tissue 22 may be internal or external body tissue. Thus, the body tissue 22 may be a portion of the skin, ligament, bone, muscle, cartilage or other component of a human body.

Method of Closure

When a discontinuity 20 in body tissue 22 is to be closed, a suture 26 is inserted through the openings or passages 52 in a plurality of anchors 24 (FIG. 4). This results in an array or series 58 of anchors 24 being disposed on the suture 26. The number of anchors 24 which are strung onto the suture 26 advantageously exceeds the number of anchors which it is anticipated may be required to close the discontinuity 20. Of course, if an insufficient number of anchors 24 is strung on the suture 26 and additional anchors are required, the suture can be inserted through the additional anchors when the discontinuity 20 is partially closed.

Once the suture 26 has been inserted through the anchors 24, the anchors are pushed through the body tissue 22 at locations which are offset along opposite sides of the discontinuity 20 (FIGS. 3 and 5). Thus, one of the anchors 24 on the suture 26 is pushed through the body tissue 22 along the left side 34 of the discontinuity 20 (FIG. 5). The next succeeding anchor 24 on the suture 26 is pressed through the body tissue along the right side 36 of the discontinuity 20 at a location which is offset along the discontinuity from the first anchor. Each of the anchors 24 on the suture 26 (FIG. 4) is pushed through the body tissue along one of the sides 34 or 36 (FIG. 1) of the discontinuity 20 so that successive anchors are at offset locations along opposite sides of the discontinuity.

The suture 26 extends through the anchors 24 as they are pushed through the body tissue 22. Thus, the suture 26 extends through the cylindrical opening 52 and across an annular leading end surface 54 (FIGS. 3 and 5) of an anchor 24 as it is pushed through the body tissue 22. The suture 26 is pulled or tensioned to move the inner side surface 44 on opposite sides 34 and 36 of the discontinuity into abutting engagement in the manner illustrated in FIG. 3. As this occurs, a portion of the suture 26 is pulled from within an opening 52 in an anchor 24.

When an anchor, for example, the anchor 24c (FIG. 5), is to be positioned along the left side 34 of the discontinuity 20, the anchor 24c is positioned in alignment with the location where it is to be pushed through the body tissue. Thus, a leading end portion 62 of the anchor 24c is positioned in engagement with the inner side surface 44 of the body tissue. At this time, the cylindrical outer side surface 48 of the anchor 24c extends perpendicular to the inner side surface 44 of the body tissue 22 along the left side 34 of the discontinuity 20. The suture 26 extends through the anchor 24c and across the annular leading end surface 54 of the anchor.

Force is applied to the anchor 24c to push the leading end portion 62 of the anchor through the inner side surface 44 of the body tissue 22. Continued movement of the leading end portion 62 of the anchor 24c through the body tissue 22 results in the leading end portion moving through the outer side surface 40 of the body tissue. Thus, once the anchor 24c has been aligned with a location where it is to be pushed through the body tissue 22 along the left side 34 of the discontinuity 20, force is applied against the trailing end portion 64 of the anchor 24, in the manner indicated by an arrow 66 in FIG. 5. The force applied against the trailing end portion 64 of the anchor 24c is effective to push the anchor through the body tissue 22.

After the anchor 24c has been pushed through the body tissue (FIG. 6), the suture 26 is pulled. As the suture 26 is tensioned, torque is applied to the leading end portion 62 of the anchor 24c to rotate the anchor from the orientation shown in FIG. 5 through the orientation shown in FIG. 6 to the position shown in FIG. 3. Although only the anchors 24a and 24c are illustrated in FIG. 6, it should be understood that the anchor 24b is disposed adjacent to the right side 36 of the discontinuity 20 in the manner illustrated in FIG. 3.

The discontinuity 20 has been shown schematically in FIG. 7 with the left and right sides of the discontinuity separated to illustrate the manner in which the suture 26 extends between the anchors 24 on the left and right sides 34 and 36 of the discontinuity. However, it should be understood that FIG. 7 is a schematic illustration. It is contemplated that it will probably be desired to pull the suture 26 as each anchor 24 in turn is positioned along a side 34 or 36 of the discontinuity.

Therefore, as each anchor in turn is positioned along a side of the discontinuity 20, the suture 26 is pulled to press the inner side surface 44 (FIG. 3) along the left side 34 of the discontinuity 20 against the inner side surface 44 along the right side 36 of the discontinuity 20. As the suture is pulled and each anchor 24 is positioned in turn along a side 34 or 36 of the discontinuity 20, the suture 26 moves in the opening or passage 52 in the anchor.

Method of Guiding Anchor

It is contemplated that a thin elongated member 72 (FIG. 8) may advantageously be used to guide movement of each of the anchors 24 in turn as the anchor is pushed through the body tissue 22. The thin elongated member 72 may be either a needle or a K-wire. Although the thin elongated member 72 has been shown in FIG. 8 as having a linear configuration, it is contemplated that the thin elongated member 72 could have a curving configuration if desired.

When the thin elongated member 72 is to be used to assist in guiding movement of anchors 24 through the body tissue 22, the thin elongated member is inserted through the central openings or passages 52 through each of the anchors 24. Although it is preferred to first insert the suture 26 through the openings 52 in the anchors 24 (FIG. 4) and then to insert the thin elongated member 72 through the openings in the anchors, the thin elongated member could be inserted through the openings in the anchors before the suture 26 is inserted through the openings in the anchors. Once the thin elongated member 72 has been inserted through the openings 52 in the anchors 24 (FIG. 8), the anchors are disposed in a linear array and are supported by the thin elongated member.

Figure 8:
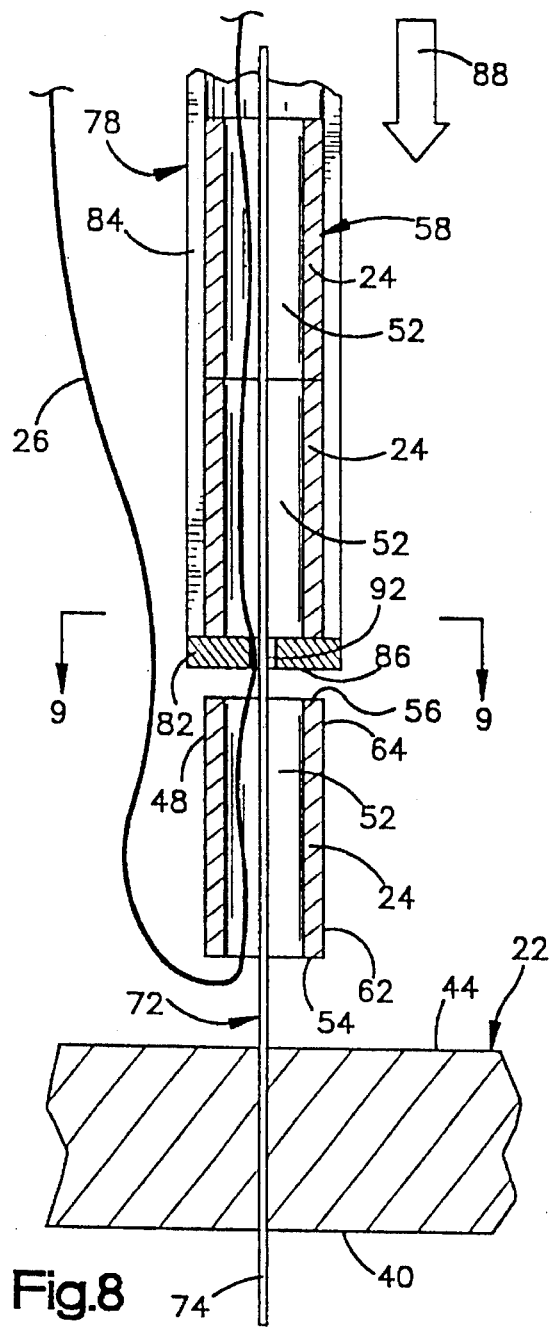
FIG. 8 is a schematic sectional view depicting a method which is similar to the method of FIGS. 1–7 and in which a thin elongated member is used to guide movement of the anchors.

The thin elongated member 72 is then inserted through the body tissue 22 with the anchors 24 disposed in a linear array on the thin elongated member (FIG. 8). A leading end portion 74 of the thin elongated member 72 is inserted through the body tissue from the inner side 44 to the outer side 40. A longitudinal central axis of the thin elongated member 72 extends perpendicular to both the inner and outer side surfaces 44 and 40 of the body tissue 22. Of course, the thin elongated member 72 may be skewed from a perpendicular with the inner and outer side surfaces 44 and 40 if desired.

Figure 10:
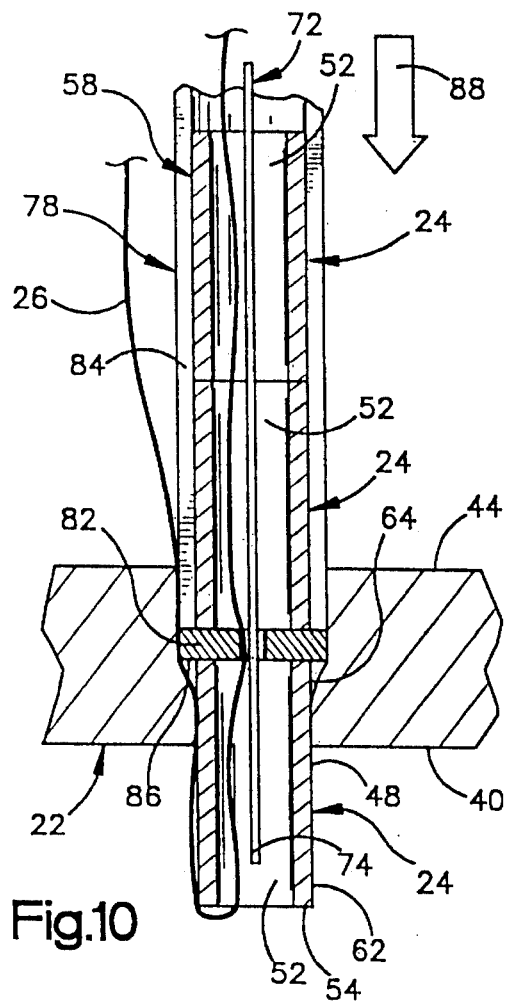
FIG. 10 is a schematic sectional view depicting the manner in which a pusher member is used to push an anchor along the thin elongated member and through the body tissue.

A leading one of the anchors 24 in the array of anchors on the thin elongated member 72 is then pushed through the body tissue 22 from the inner side 44 to the outer side 40 (FIG. 10). As this occurs, the thin elongated member 72 maintains the cylindrical outer side surface 48 of the anchor 24 in a generally perpendicular relationship with the inner side surface 44 and outer side surface 40 of the body tissue 22. Therefore, the leading end portion 62 of the anchor 24 passes through the inner side surface 44 and then the outer side surface 40 of the body tissue 22 ahead of the trailing end portion 64 of the anchor 24. As this occurs, the suture 26 extends across the leading end surface 54 and along the cylindrical side surface 48 of the anchor 24.

Once the anchor 24 has passed through the body tissue 22 (FIG. 6), the thin elongated member 72 is withdrawn from the body tissue with the remaining anchors in the array 58 of anchors on the thin elongated member and suture 26. The suture 26 is then tensioned. Tensioning the suture 26 applies a force to the leading end portion 62 of the anchor 24 to rotate the anchor in a generally counterclockwise direction (as viewed in FIG. 6). This results in the outer side surface 48 of the anchor 24 being pressed firmly against the outer side surface 40 of the body tissue 22 in the manner illustrated in FIG. 3.

Once the first anchor 24 in an array 58 of anchors on the thin elongated member 72 has been moved through and positioned relative to the body tissue 22 along one side of the discontinuity 20, the thin elongated member is inserted through the opposite side of the discontinuity. The next succeeding anchor, with the suture 26 extending through the central opening 52, is then moved along the thin elongated member 72 and through the body tissue 22 on the opposite side of the discontinuity 20. These steps are repeated until anchors 24 have been positioned along opposite sides 34 and 36 of the discontinuity 20 (FIG. 1) to close the discontinuity.

For example, if the first anchor 24 in a series 58 of anchors on the thin elongated member 72 (FIG. 8) and the suture 26 is to be inserted through the body tissue along the left side 34 of the discontinuity 20, the end portion 74 of the thin elongated member 72 is inserted through the body tissue from the inner side 44 to the outer side 40 (FIG. 8). The first anchor 24 in the series of anchors on the thin elongated member is then moved through the body tissue 22. The thin elongated member 72 is then withdrawn from the body tissue 22 along the left side 34 of the discontinuity 20.

The thin elongated member 72 is then inserted through the body tissue 22 from the inner side 44 along the opposite side, that is the right side 36, of the discontinuity 20. The next anchor 24 is inserted through the inner side surface 44 of the body tissue along the right side 36 of the discontinuity 20. Since the thin elongated member 72 and the anchors 24 are inserted from the inner side 44 of the body tissue, the inner side of the body tissue along opposite sides 34 and 36 of the discontinuity 20 are pressed into abutting engagement with each other by a force transmitted between the anchors 24 by the suture 26 in the manner illustrated in FIG. 2.

Pusher Member

A pusher member 78 (FIGS. 8, 9 and 10) may be used to push each of the anchors 24 in turn through the body tissue 22. The pusher member 78 includes a presser section 82 which is connected to one end of a semi-circular magazine section 84. The presser section 82 has a circular end surface 86 (FIG. 8) which applies force against the trailing end portion 62 of an anchor 24 to press the anchor through the body tissue 22 in the manner illustrated in FIG. 10.

The pusher member 78 is moved toward the inner side surface 44 of the body tissue 22, in the manner indicated by the arrow 88 in FIG. 8. As the lower (as viewed in FIGS. 8 and 10) side 86 of the presser section 82 pushes the leading anchor 24 through the body tissue 22 (FIG. 10), the succeeding anchors in the array 58 of anchors on the thin elongated member 72 are supported in a linear array in the magazine section 84 of the pusher member 78. The suture 26 extends through the cylindrical openings 52 in the anchors 24 and along the outer side surface 48 of an anchor being pushed through the body tissue 22 and the outer side of the pusher member 78 (FIG. 10).

After the leading anchor 24 has been pushed through the body tissue 22, the pusher member 78 and thin elongated member 72 are withdrawn together from the body tissue 22, that is, moved upwardly as viewed in FIG. 10. This results in the leading anchor 24 remaining adjacent to the outer side surface 40 of the body tissue 22. The succeeding anchors 24 remain in the array 58 in the magazine 84.

The thin elongated member is then flexed or resiliently deflected to move the next succeeding or lower (as viewed in FIG. 8) anchor outward from the magazine section 84. Thus, the thin elongated member 72 is moved radially outward of a slot 92 (FIG. 9) in the presser section 82. As this occurs, the next succeeding anchor 24 moves off of the presser section 82 and moves downward (as viewed in FIG. 8) along the suture 26 to position the next succeeding anchor for insertion through the body tissue 22. The remaining anchors 24 in the array of anchors in the magazine section 84 are then supported by the presser section 82.

Figure 9:
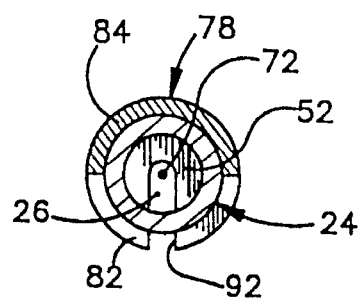
FIG. 9 is a sectional view, taken generally along the line 9—9 of FIG. 8.

Although one specific construction of the pusher member 78 has been illustrated in FIGS. 8–10, it is contemplated that the pusher member 78 could have many different constructions. Regardless of the construction of the pusher member 78, the pusher member is used to sequentially push the anchors 24 through the body tissue 22.

Alternative Method of Pushing Anchors

It is contemplated that it may be desired to eliminate the use of the pusher member 78. If this is done, force is transmitted through the series 58 (FIG. 11) of anchors 24 on the thin elongated member 72 to push the leading anchor through the body tissue 22. Thus, the leading anchor 24 is pushed through the body tissue 22 by force transmitted to a trailing end portion 64 of the leading anchor by the next succeeding anchor. After the leading anchor 24 has been pushed through the body tissue by the next succeeding anchor, the next succeeding anchor and the thin elongated member 72 are withdrawn together from the body tissue.

Figure 11:
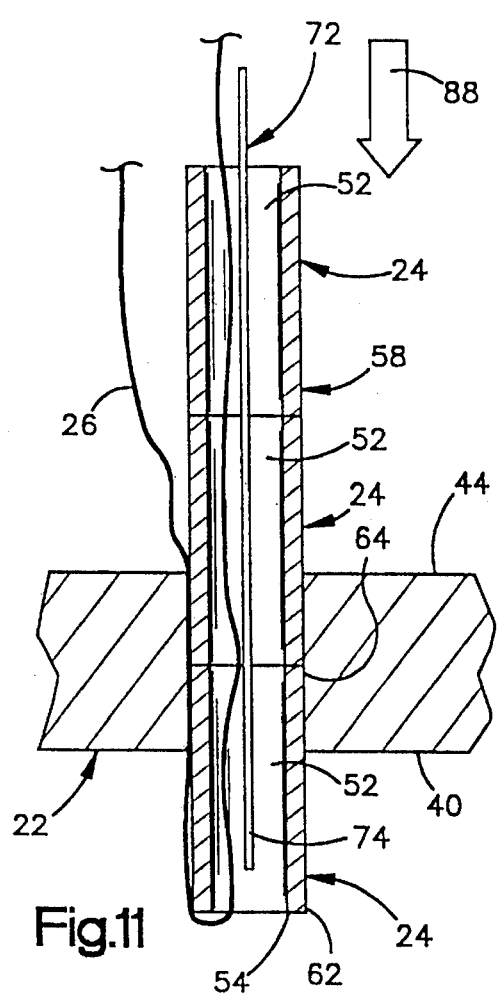
FIG. 11 is a schematic sectional view, generally similar to FIG. 10, illustrating a third method in which force is transmitted between anchors to move an anchor through the body tissue.

Although the thin elongated member 72 is illustrated in FIG. 11 as being used to guide movement of the anchors 24, the use of the thin elongated member may be dispensed with if desired. The anchors 24 may be guided by only the suture 26. Alternatively, a magazine, similar to the magazine 84 of FIGS. 8 and 9, may be used to guide movement of the anchors 24.

Alternative Method of Closure

Figure 12:
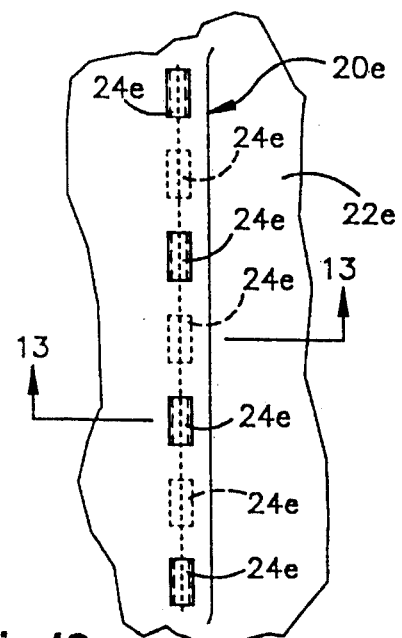
FIG. 12 is a schematic plan view, generally similar to FIG. 1, of an alternative manner of closing a discontinuity in body tissue.
Figure 13:
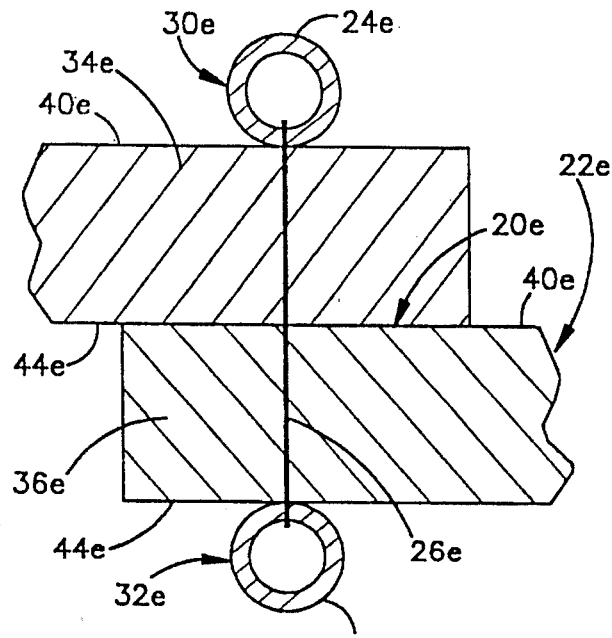
FIG. 13 is a schematic sectional view, taken along the line 13—13 of FIG. 12, further illustrating the alternative manner of closing the discontinuity.

In the embodiment of the invention illustrated in FIGS. 1–11, the discontinuity 20 is closed with the inner side surface areas pressing against each other in the manner illustrated in FIGS. 2 and 3. However, it is contemplated that the discontinuity could be closed in a different manner if desired. In the embodiment of the invention illustrated in FIGS. 12 and 13, the body tissue is overlapped with an inner side surface of the body tissue along one side of the discontinuity disposed in engagement with the outer side surface of the body tissue along the opposite side of the discontinuity. Since the embodiment of the invention illustrated in FIGS. 12 and 13 is generally similar to the embodiment of the invention illustrated in FIGS. 1–11, similar numerals will be utilized to designate similar components, the suffix letter "e" being associated with the numerals of FIGS. 12 and 13 to avoid confusion.

A discontinuity 20e in body tissue 22e is closed by anchors 24e. The anchors 24e are interconnected by a suture 26e (FIG. 13). The anchors 24e include an array 30e (FIG. 13) disposed along the outer or upper (as viewed in FIG. 13) side 34e of the discontinuity 20e and an array of anchors 32e disposed along the inner or lower (as viewed in FIG. 13) side 36e of the discontinuity. The anchors 24e in the array 30e of anchors are pressed against an outer side surface 40e of body tissue along the outer side 34e of the discontinuity 20e. The anchors 24e are pressed against the inner side 44e of body tissue 22e along an inner side 36e of the discontinuity 20e.

When the anchors 24e are sequentially positioned relative to the body tissue 22e, the anchors in the outer array 30e of anchors are pushed through the body tissue from the inner side 44e to the outer side 40e. However, the anchors 24e in the inner array 32e of anchors are pushed through the body tissue from the outer side 40e to the inner side 44e of the body tissue. Since the anchors 24e in the inner array 32e of anchors are disposed adjacent to the inner side 44e of the body tissue 22e, it is believed that it will be particularly advantageous to form the anchors 24e and the suture 26e of a material which is capable of being absorbed by body tissue so that the anchors 24e in the inner array 32e of anchors and the suture 26e do not have to be removed. Of course, the anchors 24e in the outer array 30e of anchors may also be formed of a material which is capable of being absorbed by body tissue.

Conclusion

In view of the foregoing description, it is apparent that the present invention provides a new and improved method of closing a discontinuity 20 in body tissue. When a discontinuity 20 in body tissue is to be closed, a suture 26 is inserted through openings 52 in anchors 24 to provide a series 58 of anchors on the suture. In addition, a thin elongated member 72 may be inserted through the openings 52 in the anchors.

The thin elongated member 72 is then inserted through body tissue at a first location disposed along a first side 34 of the discontinuity 20. A first anchor is then pushed through the body tissue 22 with the suture extending through the opening 52 in the first anchor. The thin elongated member 72 is then inserted through body tissue 22 at a second location disposed along a second side 36 of the discontinuity 20. A second anchor 24 is pushed through the body tissue 22 with the suture 26 extending through the opening 52 in the second anchor.

Having described the invention, the following is claimed:

1. An apparatus comprising a magazine which holds an array of anchors, said magazine having a pusher section with an outer side surface which is engagable with a trailing end of an anchor disposed outside of said magazine to apply force against the trailing end of the anchor disposed outside of the magazine, a thin elongated member extending through each of the anchors in the array of anchors in said magazine and through the anchor disposed outside of said magazine, and a suture extending through each of the anchors in the array of anchors in said magazine and through the anchor outside of said magazine.

2. An apparatus as set forth in claim 1 wherein said thin elongated member is resiliently flexible to move an anchor in the array of anchors out of the magazine.

3. An apparatus as set forth in claim 1 wherein said pusher section of said magazine has an inner side surface which is engaged by a leading anchor in the array of anchors in said magazine.

4. A method comprising the steps of positioning an array of anchors in a magazine with a thin elongated member extending through the array of anchors in the magazine and through an anchor outside of the magazine and with a suture extending through the array of anchors in the magazine and through the anchor outside of the magazine, and, thereafter, moving the anchor outside of the magazine into body tissue by pressing a leading end portion of the anchor outside of the magazine against the body tissue under the influence of force applied against a trailing end of the anchor by the magazine.

5. A method as set forth in claim 4 further including the step of moving the array of anchors in the magazine along the thin elongated member simultaneously with performance of said step of moving the anchor outside of the magazine into body tissue.

6. A method as set forth in claim 4 further including the steps of moving an anchor out of the magazine by resiliently flexing the thin elongated member.

7. A method of comprising the steps of providing a plurality of anchors, inserting a suture through a passage in each anchor of the plurality of anchors, inserting a thin elongated member through a passage in each anchor of the plurality of anchors, inserting the thin elongated member into body tissue, and moving at least one of the anchors along the thin elongated member into body tissue with the suture and the thin elongated member extending through a passage in each anchor of the plurality of anchors.

8. A method as set forth in claim 7 wherein said step of moving at least one of the anchors along the thin elongated member into body tissue includes pressing a leading end of an anchor next succeeding the one anchor against a trailing end of the one anchor.

9. A method comprising the steps of providing a plurality of anchors each of which has a passage extending between first and second ends of an anchor, inserting a suture through the passage in each of the anchors of the plurality of anchors, positioning the plurality of anchors in axial alignment with each other with the suture extending through the passages in the plurality of anchors, and moving at least a first one of the anchors into body tissue, said step of moving at least the first one of the anchors into body tissue includes moving a first end of the first one of the anchors into engagement with body tissue, pressing a first end of a second one of the anchors against a second end of the first one of the anchors while the first end of the first one of the anchors is in engagement with body tissue, and displacing body tissue under the influence of force transmitted from the second one of the anchors to the first one of the anchors and applied against body tissue by the first one of the anchors.

* * * * *